(12) United States Patent
Okoniewski

(10) Patent No.: US 8,353,819 B2
(45) Date of Patent: Jan. 15, 2013

(54) ENDOSCOPIC/LAPAROSCOPIC INTRODUCER SLEEVE

(75) Inventor: Gregory G. Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 639 days.

(21) Appl. No.: 12/594,824

(22) PCT Filed: Apr. 4, 2008

(86) PCT No.: PCT/US2008/059341
§ 371 (c)(1),
(2), (4) Date: Oct. 6, 2009

(87) PCT Pub. No.: WO2008/127886
PCT Pub. Date: Oct. 23, 2008

(65) Prior Publication Data
US 2010/0063359 A1 Mar. 11, 2010

Related U.S. Application Data

(60) Provisional application No. 60/922,856, filed on Apr. 11, 2007.

(51) Int. Cl.
*A61B 1/00* (2006.01)
(52) U.S. Cl. ........ 600/121; 600/122; 600/123; 600/124; 600/125; 600/133
(58) Field of Classification Search .......... 600/121–125
See application file for complete search history.

(56) References Cited

U.S. PATENT DOCUMENTS

| | | | |
|---|---|---|---|
| 4,593,699 A | 6/1986 | Poncy et al. | |
| 4,741,326 A | 5/1988 | Sidal et al. | |
| 4,772,275 A | 9/1988 | Erlich | |
| 4,886,049 A | 12/1989 | Darras | |
| 4,946,440 A | 8/1990 | Hall | |
| 5,088,178 A | 2/1992 | Stolk | |
| 5,167,634 A * | 12/1992 | Corrigan et al. | 604/160 |
| 5,228,851 A | 7/1993 | Burton | |
| 5,337,734 A | 8/1994 | Saab | |
| 5,363,843 A * | 11/1994 | Daneshvar | 128/897 |
| 5,406,939 A * | 4/1995 | Bala | 600/121 |
| 5,545,121 A * | 8/1996 | Yabe et al. | 600/121 |
| 5,569,161 A | 10/1996 | Ebling | |
| 5,647,857 A | 7/1997 | Anderson et al. | |
| 5,938,586 A | 8/1999 | Wilk et al. | |
| 5,989,183 A | 11/1999 | Reisdorf | |
| 6,027,480 A | 2/2000 | Davis et al. | |
| 6,051,293 A | 4/2000 | Weilandt | |
| 6,110,103 A | 8/2000 | Donofrio | |
| 6,224,543 B1 * | 5/2001 | Gammons et al. | 600/124 |
| 6,293,907 B1 * | 9/2001 | Axon et al. | 600/114 |
| 6,305,536 B1 * | 10/2001 | Tanaka | 206/316.2 |
| 6,383,209 B1 | 5/2002 | Crowley | |
| 6,749,601 B2 | 6/2004 | Chin | |
| 6,929,601 B2 * | 8/2005 | Nakao | 600/121 |
| 6,978,784 B2 | 12/2005 | Pekar | |
| 7,160,246 B2 * | 1/2007 | Humble et al. | 600/124 |
| 7,645,230 B2 * | 1/2010 | Mikkaichi et al. | 600/121 |
| 7,914,555 B2 * | 3/2011 | Nguyen et al. | 606/246 |

* cited by examiner

*Primary Examiner* — Matthew J Kasztejna

(57) ABSTRACT

A protective sleeve apparatus for protecting an endoscopic or laparoscopic instrument includes an elongated tubular member having an open proximal end and an open distal end. The elongated tubular member is sized and configured to receive a laparoscopic or endoscopic instrument therethrough. The tubular member has a folded section adjacent the distal end in releasable engagement with an intermediate section of the tubular member to define a substantially enclosed sleeve to receive the instrument and substantially prevent entry of contaminants within an interior of the tubular member. The folded section is releasable from the intermediate section upon exertion of a proximal force to the tubular member to facilitate removal of the tubular member along the instrument.

12 Claims, 5 Drawing Sheets

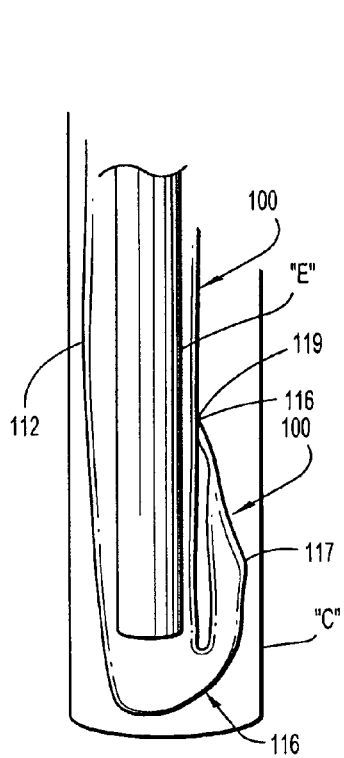
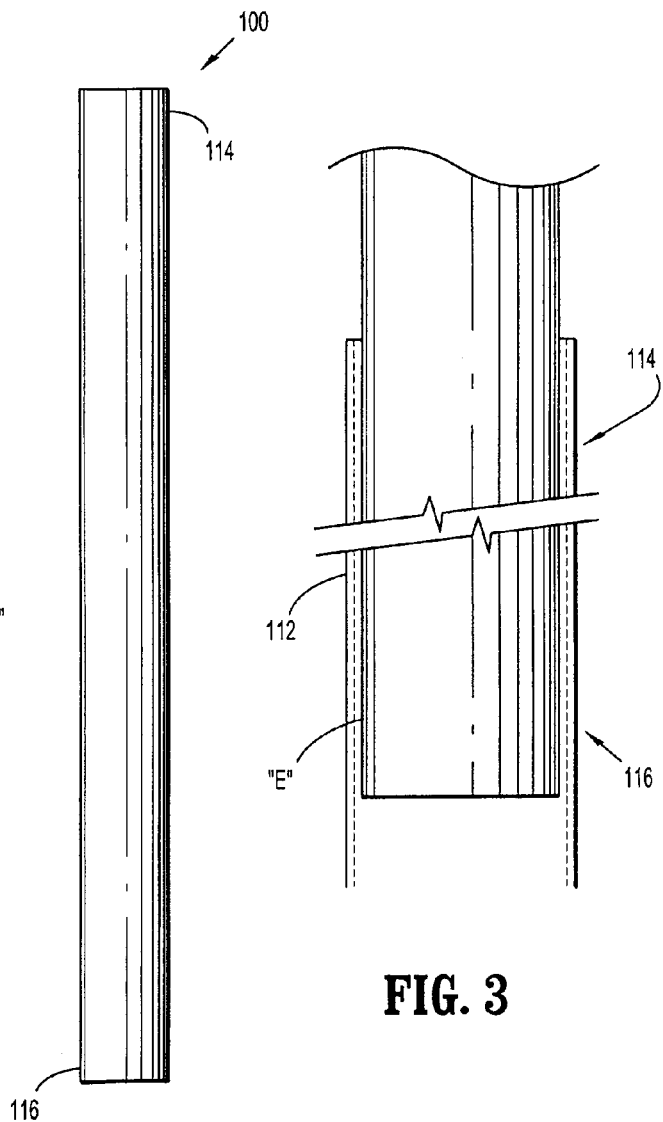
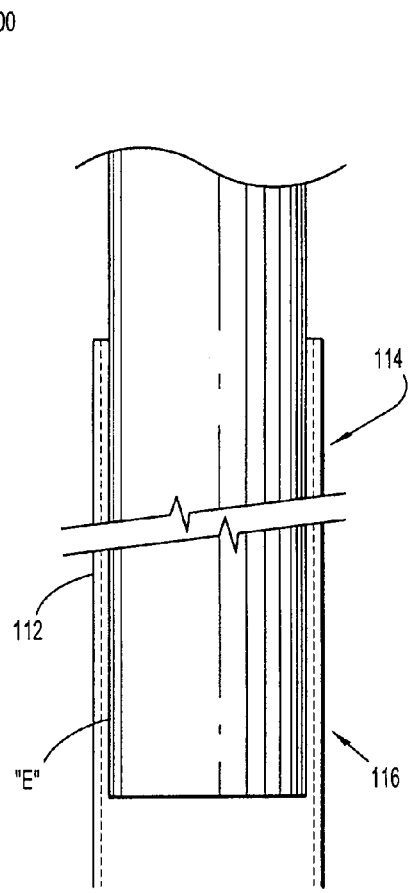
FIG. 1
FIG. 2
FIG. 3

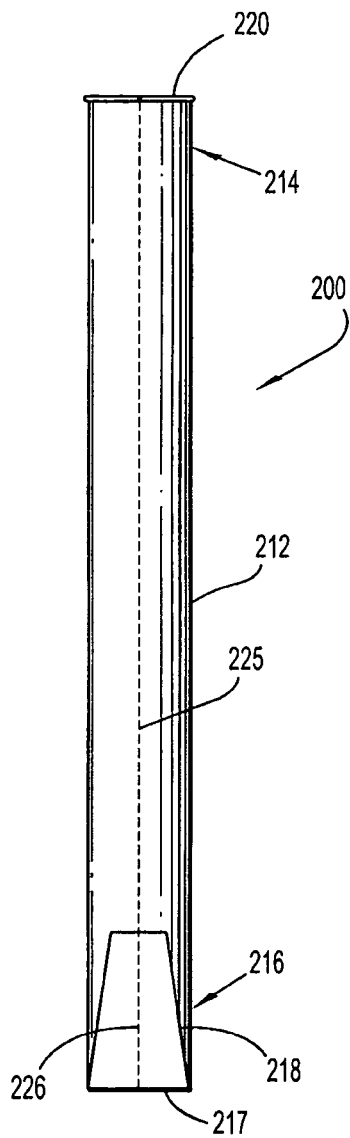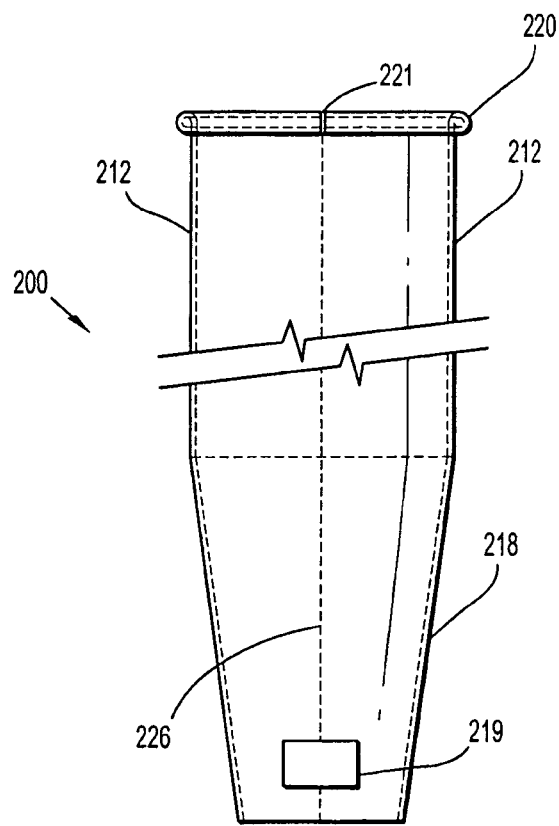
FIG. 4
FIG. 5

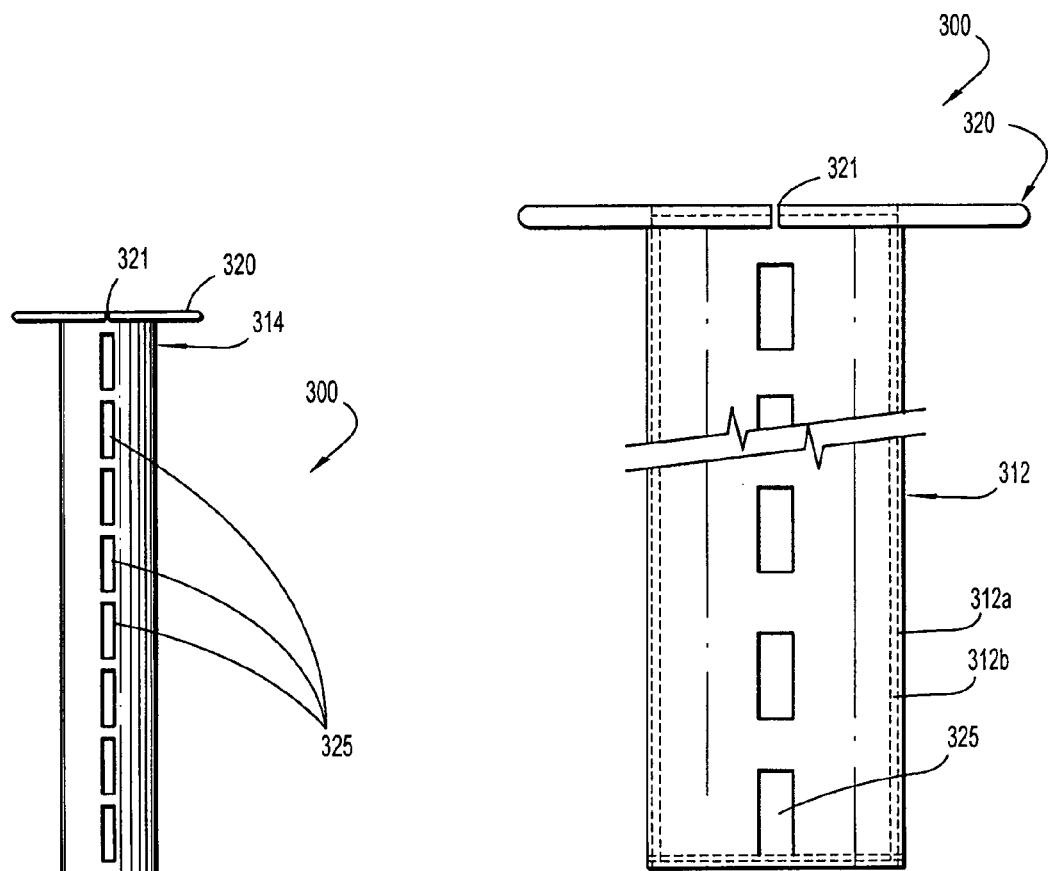
FIG. 8
FIG. 9
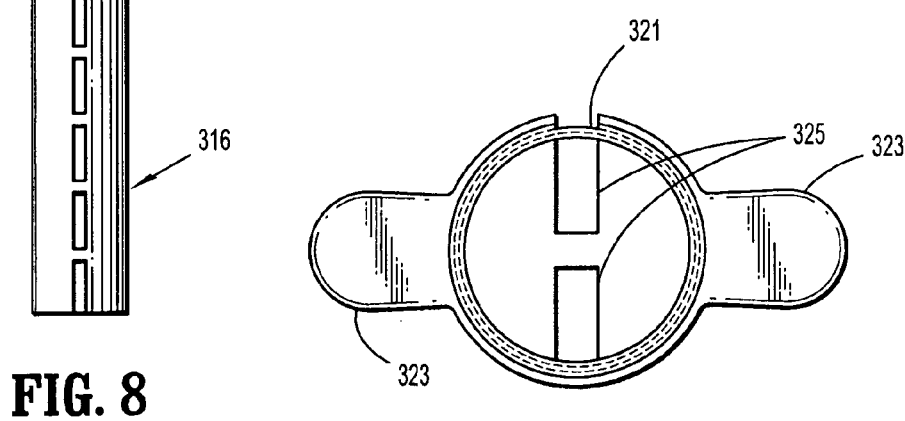
FIG. 10

ENDOSCOPIC/LAPAROSCOPIC INTRODUCER SLEEVE

CROSS REFERENCE TO RELATED APPLICATIONS

This application is a National Stage Application of PCT/US2008/059341 filed Apr. 4, 2008 under 35 USC §371 (a), which claims priority of U.S. Provisional Patent Application Ser. No. 60/922,856 filed Apr. 11, 2007 the entire contents of which are hereby incorporated by reference.

BACKGROUND

1. Technical Field

The present disclosure relates to endoscopic and laparoscopic instruments, and more particularly, relates to a sleeve for protecting endoscopes, laparoscopes, and the like, from contamination prior to and during intracorporeal introduction.

2. Background of Related Art

The use of endoscopes, laparoscopes and other similar medical instruments for diagnostic and therapeutic procedures is well known to those skilled in the art. Endoscopes, laparoscopes and the like are used for viewing virtually anywhere within the body. The term "endoscope" or "endoscopic device" will be used hereinafter when referring to any such device for viewing within the body. Endoscopes are specifically used for viewing the interior of hollow organs, such as the colon or the urethra, and within the abdominal cavity. Endoscopes generally include a fragile optic system that is prone to contamination during intracorporeal introduction. Prior to and during introduction of the endoscopic device into the body, the optical end thereof may come into contact with the cannula or trocar, seal systems, fluids, tissue, other instruments, the user or support staff, and the like. Direct contact with any of these items could cause contamination of the optic system and result in less than optimal performance from the endoscope. Once the endoscope is received within the hollow organ, abdominal cavity, or the like, the risk for contamination is reduced.

In a response to the contamination problem, and to further address the high costs and difficulty of cleansing and sterilizing these instruments between uses, it has been known to cover the distal end of the endoscopes during use with a sealed, protective sheath, sleeve or cover of various sorts and configurations. Such sleeves are commonly elongated tubular sleeves each having one open end for inserting the medical instruments and one closed, distal end. These protective sleeves remain positioned over the distal end of the endoscope for the entire procedure and are only removed from the endoscope once the procedure has been completed and the instrument has been removed from the body cavity. These sleeves are generally disposable. During procedures in which a conventional, or non-removable, sleeve is used to protect an endoscopic device, it is important to have a sleeve of proper length and diameter. The excess material present in a sleeve that is longer than necessary to properly cover a particular endoscopic device may interfere with the introduction of the endoscope into the body cavity or may otherwise negatively affect the operation of the endoscope. Any portion of the conventional sleeve in excess of that which is necessary would require the bunching-up of the sleeve along the endoscope. This bunching up may interfere with the surgical procedure, or worse yet, lead to contamination of the surgery site and infection. Alternatively, the excess length of the conventional sleeve could be cut away and removed adding unnecessary steps to an already complicated procedure.

A conventional sleeve of a diameter in excess of what is necessary may also negatively affect the operation and optical performance of the endoscopic device. Operationally, the folding or bunching of the sleeve created by the excess sheath material may affect the ability of a user to manipulate the endoscopic device during viewing. Additionally, the folding or bunching created by the larger than necessary diameter may negatively affect the integrity of the seal between the device and the trocar or other access means. The folding or bunching of the sleeve may distort the image or otherwise negatively affect the viewing. Thus, a conventional, non-removable sleeve of an appropriate diameter is necessary for successful operation of the endoscopic device and clear viewing within the body cavity.

Regardless of its size or configuration, the sleeve must be comprised of an optically transparent material, or include an optically transparent window for viewing therethrough. As used herein, the term "optically transparent" means capable of transmitting visible light so that an object may be clearly seen therethrough with little or no distortion. For sleeves used with endoscopes configured for viewing along the longitudinal axis of the scope, the viewing window is located at the distal end of the sleeve, while endoscopes configured for viewing other than along the longitudinal access, e.g. perpendicular to the axis, require the window to be positioned in a sidewall. The use of endoscope with a protective sleeves thereon, regardless of the optical transparency of the sleeve, increases the likelihood of optical distortion, interference, poor video quality, and the like. However, as noted above, the risk for contamination of the optic system is reduced once the endoscope has been received within the body cavity; thus, once intracorporeal introduction has been achieved the need for a protective sleeve is diminished. Unfortunately, because the sleeve ends up within the body cavity along with the distal end of the endoscope, it is not possible to remove the sleeve without removing the endoscope from with the body cavity.

Therefore, it would be beneficial to have a sleeve for protecting an endoscopic device that could be removed once the device has been received and properly positioned within the targeted body cavity.

SUMMARY

In one embodiment, a protective sleeve apparatus for protecting an endoscopic or laparoscopic instrument includes an elongated tubular member having an open proximal end and an open distal end. The elongated tubular member is sized and configured to receive a laparoscopic or endoscopic instrument therethrough. The tubular member has a folded section adjacent the distal end in releasable engagement with an intermediate section of the tubular member to define a substantially enclosed sleeve to receive the instrument and substantially prevent entry of contaminants through the distal end and within an interior of the tubular member. The folded section is releasable from the intermediate section upon exertion of a proximal force to the tubular member to facilitate removal of the tubular member along the instrument.

In another embodiment, a protective sleeve apparatus for protecting an endoscopic or laparoscopic instrument includes an elongated tubular member having an open proximal end and a closed distal end. The elongated tubular member is sized and configured to receive a laparoscopic or endoscopic instrument therethrough. The elongated tubular member includes a tear line between the proximal and distal ends thereof for facilitating removal of the tubular member from the laparoscopic or endoscopic instrument. The closed distal end is formed by heating, bonding, or sealing the distal end of the tubular member. Alternatively, the closed distal end is formed by folding the tubular member upon itself to define a folded section. The folded section may be releasably affixed to an intermediate section of tubular member.

Preferably, the tubular member is substantially cylindrical. The distal end of the tubular member may be tapered. A base member may be mounted about the open proximal end of the tubular member. The base member may be in the form of a semi-rigid flexible ring. The base member may include a break. The break in the base member may be aligned with the tear line. The base member may be further configured such that the tubular member may be rolled thereon. As a further alternative, the base member includes one or more tabs for facilitating installation and removal of the tubular member.

The tubular member may include a plurality of raised ribs along its outer surface. The raised ribs are dimensioned to maintain a predetermined spacing between the tubular member and a portal through which the tubular member and instrument are introduced.

A method of using a removable sleeve for protecting an endoscopic or laparoscopic instrument is also disclosed. The method includes the steps of:

providing a sleeve capable of being removed from an endoscopic or laparoscopic device while the device is positioned within a body cavity;

installing the sleeve about the distal end of an endoscopic or laparoscopic device;

introducing the endoscopic or laparoscopic device, with the sleeve disposed thereon, through a portal accessing a body cavity;

once positioned with the body cavity, applying a pulling force to the proximal end of the sleeve; and removing the sleeve from about the endoscopic or laparoscopic device.

BRIEF DESCRIPTION OF THE DRAWINGS

The foregoing summary, as well as the following description of the embodiments will be better understood when read in conjunction with the appended figures. For the purpose of illustrating the present disclosure, several embodiments are shown. It is understood, however, that the present disclosure is not limited to the precise arrangement and instrumentalities shown.

FIG. 1 is a cross sectional side view of an endoscopic sleeve in accordance with the present disclosure disposed about the distal end of an endoscope "E" and received within a cannula "C";

FIG. 2 is a perspective view of the sleeve of FIG. 1;

FIG. 3 is an enlarged cross-sectional side view of the sleeve of FIGS. 1 and 2 disposed about the distal end of an endoscope "E";

FIG. 4 is a cross sectional side view of an alternate endoscopic sleeve in accordance with the present disclosure;

FIG. 5 is an enlarged perspective view of the proximal and distal ends of the endoscopic sleeve of FIG. 4;

FIG. 8 is a perspective view of an alternate embodiment of the present disclosure;

FIG. 9 is an enlarge perspective view of the proximal and distal ends of the endoscopic sleeve of FIG. 8;

FIG. 10 is an end view of the endoscopic sleeve of FIGS. 9 and 10;

DESCRIPTION OF THE EMBODIMENTS

Figure 6:
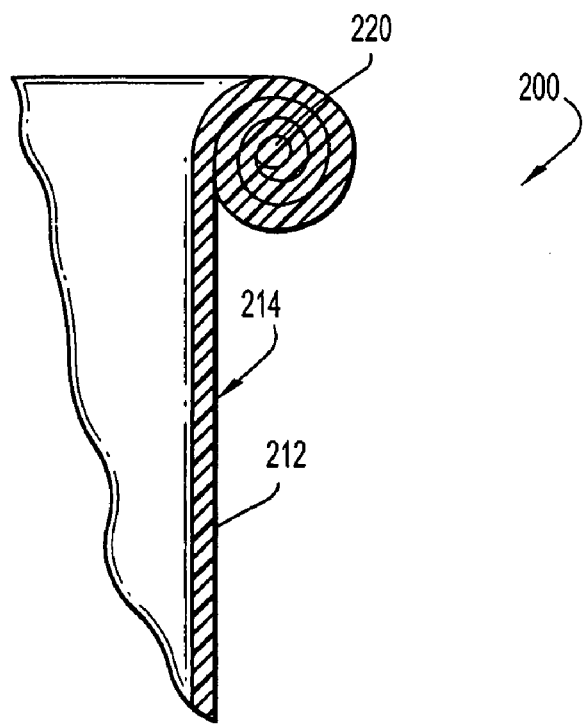
FIG. 6 is an enlarged cross-sectional side view of a portion of the proximal end of the endoscopic sleeve of FIGS. 1 and 2.
Figure 7:
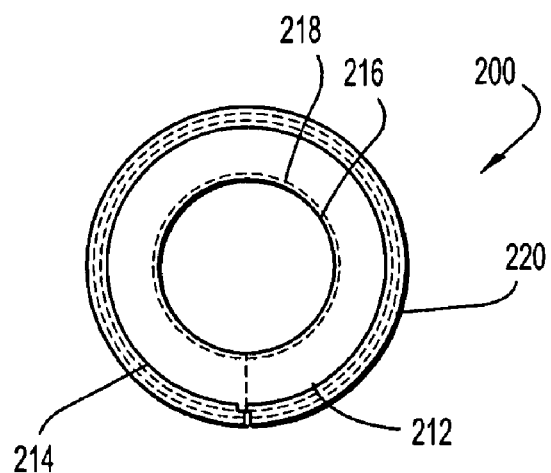
FIG. 7 is an end view of the endoscopic sleeve of FIGS. 4-6.

Referring now to the drawings wherein like reference numerals illustrate similar components throughout the several views. FIGS. 1-3 illustrate a disposable sleeve 100 in accordance with the principles of the present disclosure. In FIG. 1, sleeve 100 is disposed about the distal end of an endoscope "E" received within a cannula "C". Sleeve 100 includes an elongated annular sidewall 112 having an open proximal end 114. The distal end 116 of sleeve 100 may be closed to prevent entry of contaminate within the interior of the sleeve 100. The closed distal end may be affected by bonding, folding, or by virtue of the integrated geometry of the sleeve 100. In one embodiment, the distal end 116 is folded along fold line 117 in a manner to be discussed herein below.

Sleeve 100 may be comprised of a plastic, polymer, or the like. Sleeve 100 may be opaque, however, is preferably at least partially optically transparent. Sleeve 100 not need be optically transparent because it is removed from the distal end of an endoscopic device prior to viewing within the body cavity. However, it may be useful for sleeve 100 to be at least partially transparent so the user may ensure that the endoscopic device has been properly received within the target body cavity.

The diameter of sleeve 100 may range from about 0.5-40 mm, preferably from about 3-20 mm. Smaller diameter sleeves may be selected to accommodate smaller diameter medical devices. Preferably, sleeve 100 has a diameter of sufficient width to achieve a relatively close-fitting relationship with a particular endoscopic device. Sidewall 112 may be of any thickness. Sidewall 112 is preferably sufficiently thin and partially transparent and/or sufficiently thick to offer protection against contamination during intracorporeal introduction of the endoscopic device. In an alternate embodiment, sleeve 100 may be of sufficient thickness to provide protection against structural damage to the endoscope device from contact with the cannula, trocar, seal systems, other instruments, the user or support staff, and the like, as it is inserted into the body.

Sidewall 112 is linear and of substantially uniform diameter (i.e. a cylindrical configuration). For certain applications, it may be desirable to have a somewhat larger diameter proximal end with sidewall 112 smoothly tapering to a smaller diameter distal end (i.e. a frustro-conical configuration). The length of sleeve 100 may vary in accordance with the length of the medical instrument to be covered and the remoteness of the body cavity to be viewed. Sleeves ranging in length from about one-quarter inch to one or more feet are contemplated by the present disclosure.

Referring to FIG. 1, distal end 116 of sleeve 100 is shown in a folded and sealed condition. Distal end 116 is folded to provide a folded section 117 to effectively close and seal sleeve 100 thereby preventing entry of contaminants or the like. Folded section 117 may be releasably affixed to sidewall 112 using an adhesive 219 (FIG. 5). Alternatively, folded section 117 may be releasably affixed to sidewall 112 using any known means, including bonding, mechanical fasteners and the like. Once the protected endoscopic device has been received though the cannula and is positioned within the targeted body cavity, a proximal force is exerted on sleeve 110 which breaks the bond of the folded section 117 thereby effectively opening the distal end for removal over the endoscope as depicted in FIG. 3. Sleeve 100 may be completely retracted from about the portion of the endoscopic device received within the body. Once removed from with cannula "C", sleeve 100 may be cut away from the endoscopic device. Alternatively, and as will be described below, sleeve 100 may include tear lines (FIGS. 4-7, 11, 12) or stress riser geometry (FIGS. 8-10) to assist in removal of sleeve 100 from about the endoscopic device.

Referring now to FIGS. 4-7, in an alternate embodiment, distal end 216 of sleeve 200 tapers to form a tapered portion 218. Tapered portion 218 may be configured to more securely fit around the distal end of an endoscopic device. Sidewall 212 of sleeve 200 includes a tear line 225 formed along the length of sleeve 200. Tear line 225 may include a score line, perforations, or a linear weakened section which traverses the length of sleeve 200 from proximal end 214 through distal end 216. A linear weakened section may include an area of reduced thickness of the material of sleeve 100 or an area weakened through the application of a chemical substance to the sleeve 100. Tear line 225 is configured such that when a pulling, lateral and/or twisting force is applied to proximal end 214, the tension created along sleeve 200 causes sidewall 212 to tear along tear line 225. Tear line 225 may further be configured such that no fluid or other contaminate may penetrate sidewalls 212 therethrough. In an alternate embodiment, tear line 225 may be coated with a substance to ensure a proper seal along the tear line 225. Sleeve 200 may include one or more tear lines 225 traversing the length of sidewall 212. The one or more tear lines 225 may be configured in any suitable manner for permitting sleeve 200 to be removed from the endoscopic device from which it is protecting. Tapered portion 218 includes one or more tear lines 226, at least one of which aligns with a corresponding tear line 225 formed in sidewall 212. Tapered portion 218 may also be configured to aid in the removal of sleeve 200 from an endoscopic device after the device has been positioned within the targeted body cavity. For example, a proximal force may be applied to sleeve 200 which causes tapered portion 218 to unfold to the position depicted in FIG. 5. Continued proximal movement of sleeve 200 causes the tapered portion 218 to encounter the outer surface of the endoscopic device. In this manner, the distal end of the endoscopic device will expand tapered portion 218 and result in the tearing thereof along tear line 226, and continued tearing along tear line 225.

Referring now to FIGS. 5 and 6, proximal end 214 of sleeve 200 includes a base member 220. Base member 220 defines a circular ring configured to be secured to the proximal end of sidewalls 212. Base member 220 may be formed of a polymer, plastic, metal, or other like substance. Base member 220 is at least semi-rigid and preferably flexible. Base member 220 may include a slit or break 221 formed in the circular ring to allow base member 220 to be opened. Break 221 may be configured to be selectively separated by a user. Break 221 aligns with tear line 225 in sidewall 212. Base member 220 may be secured to sidewall 212 using any conventional means, including adhesives, friction-fitting, bonding or the like. Base member 220 may alternately be integral formed with and/or encapsulated within sidewall 212.

With particular reference to FIG. 6, sleeve 200, and more particularly, sidewall 212, may be rolled about base member 220. Depending on the thickness of sleeve 200 and the configuration of base 220, sleeve 200 may be completely rolled about and supported on base 220. A sleeve 200 of any length may be may be rolled and supported in the manner. By supporting sleeve 200 about base 220, sleeve 200 may be unrolled along the endoscopic device.

In operation, once an endoscopic device having a sleeve 200 disposed thereon has been properly received within a cannula, base 220 may be grasped to assist in removing sleeve 200 from within the cannula. As sleeve 200 is being pulled, base 220 may be twisted at break 221 to separate base 220 and facilitate longitudinal tearing of sleeve 200 along tear line 225. As sidewall 212 and tapered portion 218 longitudinally tear along tear lines 225, 226, respectively, sleeve 200 may be removed from about the endoscopic device and withdrawn from within the cannula or trocar through which it is inserted, without removing the device therefrom.

Referring now to FIGS. 8-10, in an alternate embodiment of the present disclosure, sleeve 300 includes sidewall 312 forming an open distal end 314 and closed distal end 316. Unlike sleeve 300, closed distal end 316 of sleeve 300 does not taper, is not folded and is sealed by means of bonding, adhesives, integrated geometry or the like. Also, sidewall 312 of sleeve 300 incorporates stress riser geometry to facilitate lengthwise tearing of sleeve 300. For example, sidewall 312 is configured with depressions or thinned regions 325 aligned along a length of sleeve 300 to allow sleeve 300 to be removed from about an endoscopic device after it has been inserted through a cannula or trocar into a body cavity. Depressions 325 may vary in depth according to the thickness of sidewall 312 and the material from which sleeve 300 is constructed. Depressions 325 may also vary in width and length. Preferably depressions 325 are of a thickness such that sleeve 300 is able to withstand mounting about an endoscopic device and inserted into a body cavity without tearing, yet may be torn when a longitudinal pulling force is exerted on proximal end 314.

In some applications it may be desirable for at least a portion of sleeve 300 to include multi-layer sidewalls 312a, 312b. Such multi-layer sidewalls 312a, 312b can be utilized to provide enhanced reliability or durability. By using different materials for different layers sleeve 300 may be custom-tailored to have properties to satiate a particular requirement. For example, it may be desirable to choose an inner sidewall of a very high strength polymer in combination with an outer sidewall of a very slippery polymer to facilitate insertion of the covered endoscope into the body.

Sleeve 300 further includes a base or tab portion 320 similar to base 220 of sleeve 200. Base 320 forms a circular ring configured to be secured to the open proximal end 314 of sleeve 300. Base 320 may be secured to sidewall 312 using any known means including adhesives, friction fit, bonding or the like. Base member 320 may alternately be integral formed with and/or encapsulated within sidewall 312. Base 320 may include one or more tabs 323 for assisting a user in disposing of sleeve 300 about an endoscopic device and for assisting in removal of sleeve 300 therefrom. Like base 220, base 320 includes a slit or break 321 about the circular ring to facilitate in the tearing of sidewall 312 along depressions 325.

Figures 11, 12:
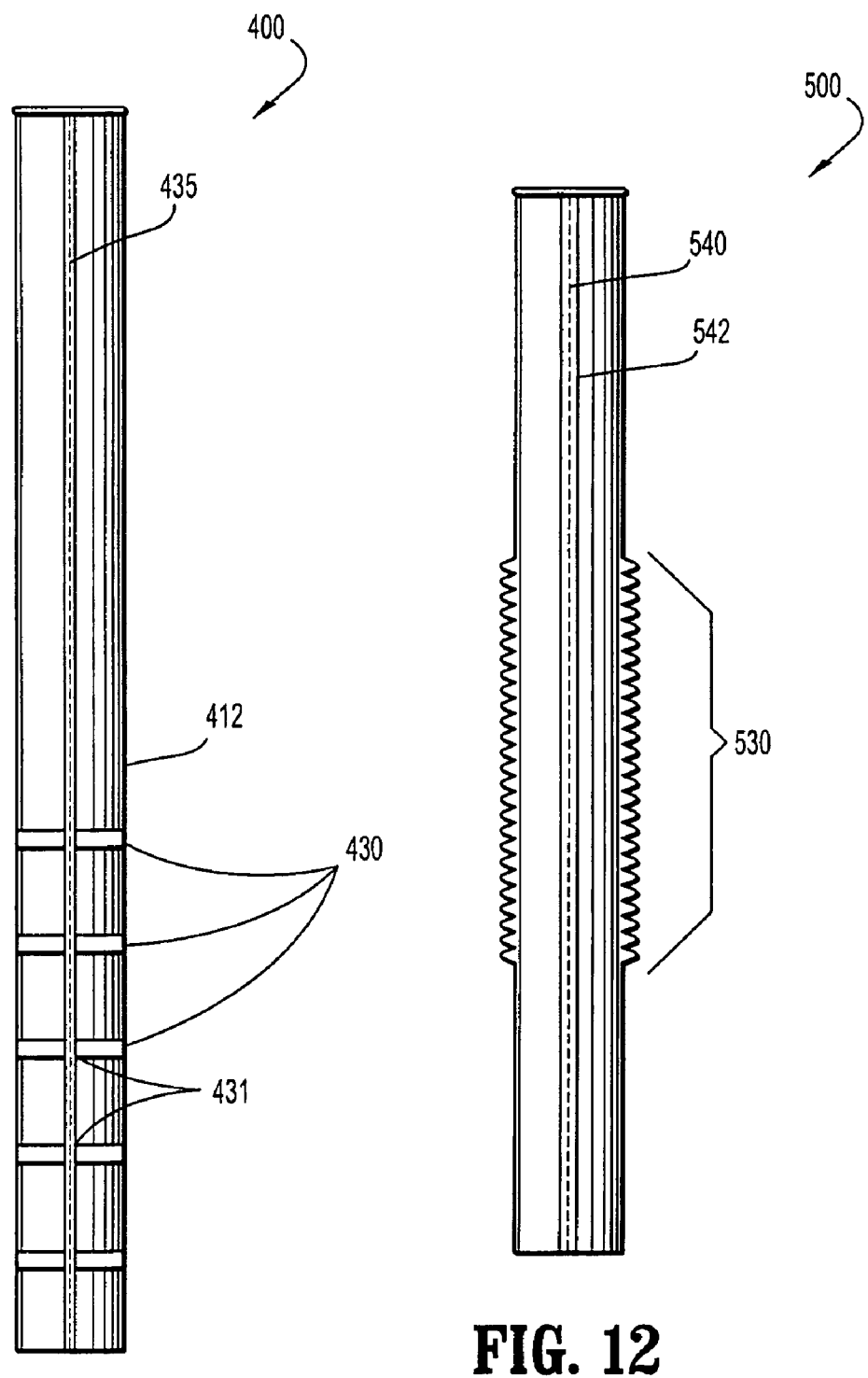
FIG. 11 is a perspective view of another embodiment of the present disclosure.
FIG. 12 is a perspective view of yet another embodiment of the present disclosure.

Referring now to FIG. 11, in an alternate embodiment of the present disclosure, sleeve 400 includes a sidewall 412 having raised ribs 430. Ribs 430 partially encircle at least a portion of sleeve 400. Ribs 430 are preferably composed of a semi-rigid flexible material, including plastic, polymers and the like. Ribs 430 may be integrally formed within sidewall 412. Ribs 430 may instead be fixedly attached to sidewall 412 using adhesives, bonding, or the like. Ribs 430 include breaks or slits 431 for facilitating removal of sleeve 400 from about the distal end of an endoscopic device. Slits 411 are in alignment with tear line 435. Ribs 430 may assist in the installation of sleeve 400 about an endoscopic device. Ribs 430 may further assist in protecting the endoscopic device from damage, by, e.g., maintaining an appropriate spacing of the endoscopic device relative to the internal wall of the cannula.

Turning now to FIG. 12, in yet another embodiment of the present disclosure, sidewall 512 of sleeve 500 may include an accordion-like portion 530. This configuration may enhance the flexibility of sleeve 500 and facilitate installation onto the endoscopic device and articulation of the device into position. In addition, tear line 540 may include perforations or the like and may further have a coating 542 applied along the tear line 540 to substantially seal the perforation.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims append hereto.

What is claimed is:

1. A protective sleeve apparatus for protecting an endoscopic or laparoscopic instrument, which comprises:

an elongated tubular member having an open proximal end and a selectively open distal end, the elongated tubular member being sized and configured to receive a laparoscopic or endoscopic instrument therethrough, the tubular member having a folded section adjacent the distal end in releaseable engagement with an intermediate section of the tubular member to define a substantially enclosed sleeve to receive the instrument and substantially prevent entry of contaminants within an interior of the tubular member, the folded section being releasable from the intermediate section upon exertion of a proximal force to the tubular member to facilitate opening of the distal end and removal of the tubular member along the instrument.

2. The protective sleeve apparatus of claim 1, wherein the folded section is formed by folding the tubular member upon itself.

3. The protective sleeve apparatus of claim 1, wherein the tubular member is substantially cylindrical.

4. The protective sleeve apparatus of claim 1, wherein the distal end of the tubular member is tapered.

5. The protective sleeve apparatus of claim 1, further including a base member mounted to the open proximal end of the tubular member.

6. The protective sleeve apparatus of claim 5, wherein the base member forms a semi-rigid flexible ring.

7. The protective sleeve apparatus of claim 6, where the base member includes a break.

8. The protective sleeve apparatus of claim 7, wherein the break in the base member is aligned with the tear line.

9. The protective sleeve apparatus of claim 5, wherein the base member is configured such that the tubular member may be rolled thereon.

10. The protective sleeve apparatus of claim 5, wherein the base member includes one or more tabs for facilitating installation and removal of the tubular member.

11. The protective sleeve apparatus of claim 1, wherein the tubular member includes a plurality of raised ribs along its outer surface, the raised ribs dimensioned to maintain a predetermined spacing between the tubular member and a portal through which the tubular member and instrument are introduced.

12. The protective sleeve apparatus of claim 1, wherein the folded section is releasably affixed to an external surface of the intermediate section of the tubular member.

\* \* \* \* \*